(12) United States Patent
Wang et al.

(10) Patent No.: US 6,451,533 B1
(45) Date of Patent: Sep. 17, 2002

(54) FLDA GENE AND METHODS FOR DETECTING PREDISPOSITION TO MUCOSA-ASSOCIATED LYMPHOID TISSUE LYMPHOMA OF THE STOMACH

(75) Inventors: Jin-Town Wang; Chih-Shen Chang; Li-Tzong Chen; Jyh-Chin Yang; Jaw-Tow Lin; Kai-Chih Chang, all of Taipei (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/522,433

(22) Filed: Mar. 9, 2000

(51) Int. Cl.[7] .................................................. C12Q 1/68
(52) U.S. Cl. .............................. 435/6; 435/91.2; 435/5; 536/23.1
(58) Field of Search .............................. 435/5, 6, 91.2; 536/23.1

(56) References Cited

U.S. PATENT DOCUMENTS 5,403,924 A    4/1995   Cover et al. ................ 536/23.1

OTHER PUBLICATIONS

Cover et al. Gastroenterology. 1999. vol. 117, No. 1, pp. 257–260.*
Liu et al. Gastroenterology. 2000. vol. 118, No. 5, pp. 988–989.*
Chang et al., "Isolation of a *Helicobacter Pylori* Protein, FldA, Associated with Mucosa–Associated lymphoid Tissue Lymphoma Of the Stomach", Gastroenterology 117:82–88, 1999.

* cited by examiner

*Primary Examiner*—Jeffrey Fredman
*Assistant Examiner*—Juliet Einsmann
(74) *Attorney, Agent, or Firm*—Fish & Richardson P.C.

(57) ABSTRACT

The present invention relates to a *Helicobacter pylori* gene, fldA, a putative flavodoxin gene and whose expression is associated with mucosa-associated lymphoid tissue lymphoma of the stomach (MALToma). A G insertion at position 481 of the fldA gene was more frequently observed in strains associated with MALToma than other strains. Therefore, the present invention provides a new method to identify *H. pylori* patient with higher risk of developing gastric MALToma.

3 Claims, 5 Drawing Sheets

```
1   ATGGGAAAAATTGGTATCTTTTTGGGACAGACAGCGGAAACGCTGAAGCTATCGCTGAA
     M  G  K  I  G  I  F  F  G  T  D  S  G  N  A  E  A  I  A  E
61  AAAATCAGCAAGGCTATTGGTAATGCTGAAGTGATTGATGTGGCTAAAGCTTCTAAAGAG
     K  I  S  K  A  I  G  N  A  E  V  I  D  V  A  K  A  S  K  E
121 CAATTTGATAGCTTTACAAAGGTTATTTTGGTCGCTCCAACAGCGGGTGCGGGCGATTTG
     Q  F  D  S  F  T  K  V  I  L  V  A  P  T  A  G  A  G  D  L
181 CAAGCAGATTGGGAAGACTTTTTAGGCACGCTAGAAGCGAGCGATTTTGCGAATAAAACC
     Q  A  D  W  E  D  F  L  G  T  L  E  A  S  D  F  A  N  K  T
241 ATTGCTCTTGTAGGCTTGGGCGATCAAGACACTTACAGCGAAACTTTTGCAGAAGGCATT
     I  A  L  V  G  L  G  D  Q  D  T  Y  S  E  T  F  A  E  G  I
301 TTCCACATTTATGAAAAAGCCAAAGCCGGCAAGGTGGTAGGGCAAACTCCCACTGATGGT
     F  H  I  Y  E  K  A  K  A  G  K  V  V  G  Q  T  P  T  D  G
361 TATCATTTCGAAGCTTCTAAAGCGGTAGAAGGCGGTAAATTCGTGGGTCTTGTGATTGAT
     Y  H  F  E  A  S  K  A  V  E  G  G  K  F  V  G  L  V  I  D
421 GAAGACAATCAAGACGATCTCACTGATGAGAGGACTTCAAAATGGGTAGAACAAATTAAA
     E  D  N  Q  D  D  L  T  D  E  R  T  S  K  W  V  E  Q  I  K
481 GGTTCTTTCGCTTAATCTTTATAAGCCCTATATTTTAGGGCTTTTTTAACTCCTTTTA
     G  S  F  A  ↑
                  V  L  S  L  N  L  Y  K  P  Y  I  L  G  L  F  ↑
541 TATCTTTCTT
```

FLDA GENE AND METHODS FOR DETECTING PREDISPOSITION TO MUCOSA-ASSOCIATED LYMPHOID TISSUE LYMPHOMA OF THE STOMACH

FIELD OF THE INVENTION

The present invention relates to a *Helicobacter pylori* gene whose expression is associated with mucosa-associated lymphoid tissue lymphoma of the stomach (MALToma), and the use of the DNA composing the gene and the protein encoded by the DNA for detecting predisposition to MALToma.

BACKGROUND OF THE INVENTION

*Helicobacter pylori*, a spiral gram-negative bacterium, was first isolated in 1982 from the gastric mucosa of a patient with gastritis and peptic ulceration (Marshall B. J. and Warren J. R., *Lancet*, 1984, 1:1311–1315). Since then, there is strong evidence showing that *H. pylori* is the causative agent of chronic active gastritis and has an important role in duodenal ulcerogenesis (Blaser M. J., *Sci. Am.*, 1996, 274:104–107). It has been documented that the relapse rate of both duodenal and gastric ulcers decreases dramatically after eradication of *H. pylori*, and cure of this chronic relapsing disease (Graham D. Y. et. al., *Ann. Intern. Med.*, 1992, 116:705–708; Hentschel E. et. al., *N. Engl. J. Med.*, 1993, 328:308–312). The infection by *H. pylori* has also been shown to be associated with adenocarcinoma and mucosa-associated lymphoid tissue lymphoma of the stomach (Nomura A. et. al., *N. Engl. J. Med.*, 1991, 325:1132–1136; Parsonnet J. et. al., *N. Engl. J. Med.*, 1991, 325:1127–1131; Bayerdorffer E. et. al., *Lancet*, 1995, 345:1591–1594). Although the prevalence of this infection and MALToma is high, only a few infected subjects develop clinically significant diseases. Most patients remain asymptomatic (Blaser M. J., *Sci. Am.*, 1996, 274:104–107).

To eradicate the infection in all patients is not feasible in terms of cost, compliance, and possible drug resistance. In addition, variation in host genetic background, environmental factors, and virulence of the bacterial strains may contribute to different clinical outcomes (Blaser M. J., *Sci. Am.*, 1996, 274:104–107). Therefore, it would be useful to find a candidate marker to differentiate the strains that are more harmful to the host. Hence, the inventors of the present application have tried to find a specific antigen of *H. pylori* associated with gastric MALToma using an immunoscreening strategy.

An objective of the invention is to identify specific antigen(s) from *H. pylori* strains associated with gastric MALToma, which seems to depend on the stimulation of *H. pylori*.

Another objective of the invention is to use the gastric MALToma associated protein, FldA, and its encoding DNA, including its mutant forms, to identify patients with higher risk of developing gastric MALToma.

Still another objective of the invention is to use antibodies against FldA or its truncated protein as a serological marker to screen for patients infected with *H. pylori* that are in high risk of developing gastric MALToma.

SUMMARY OF THE INVENTION

The present invention provides methods for screening patients infected with *H. pylori* that are in high risk of developing gastric MALToma by the following:

1) using antibodies against the surface antigens, FldA, of *H. pylori*;

2) using molecular biology techniques, such as DNA sequencing, DNA probe, gene chip, RT-PCR, or Southern hybridization, to detect the expression of fldA; and 3) using the mutation of the fldA gene of *H. pylori* to detect gastric MALToma at early stage.

In one of the preferred embodiments, the present invention discloses a method of using a FldA protein for screening patients infected with *Helicobacter pylori* that are in a high risk of developing mucosa-associated lymphoid tissue lymphoma of the stomach comprising contacting antibody-containing samples from patients with a 19-kilodalton FldA protein from *Helicobacter pylor*.

Preferably, said 19-kilodalton FldA protein is encoded by a putative flavodoxin gene (fldA) from *Helicobacter pylori* having a guanidine insertion at a position of 481.

Preferably, an ELISA method or a Western blot method is used to detect the presence of said 19-kilodalton FldA protein in said antibody-containing samples from patients.

Preferably, said antibody-containing samples from patients contain antibodies which are polyclonal or monoclonal antibodies.

In another preferred embodiments, the present invention discloses a method of using a putative flavodoxin gene (fldA) from *Helicobacter pylori* for screening patients infected with *Helicobacter pylori* that are in a high risk of developing mucosa-associated lymphoid tissue lymphoma of the stomach comprising using a molecular biology technique to detect the expression of fldA gene of *Helicobacter pylori* from patients so that a guanidine insertion at a position of 481 of said fldA gene can be determined.

Preferably, said molecular biology technique is DNA sequencing, DNA probe, gene chip, RT-PCR, or Southern hybridization.

Figure 4A:
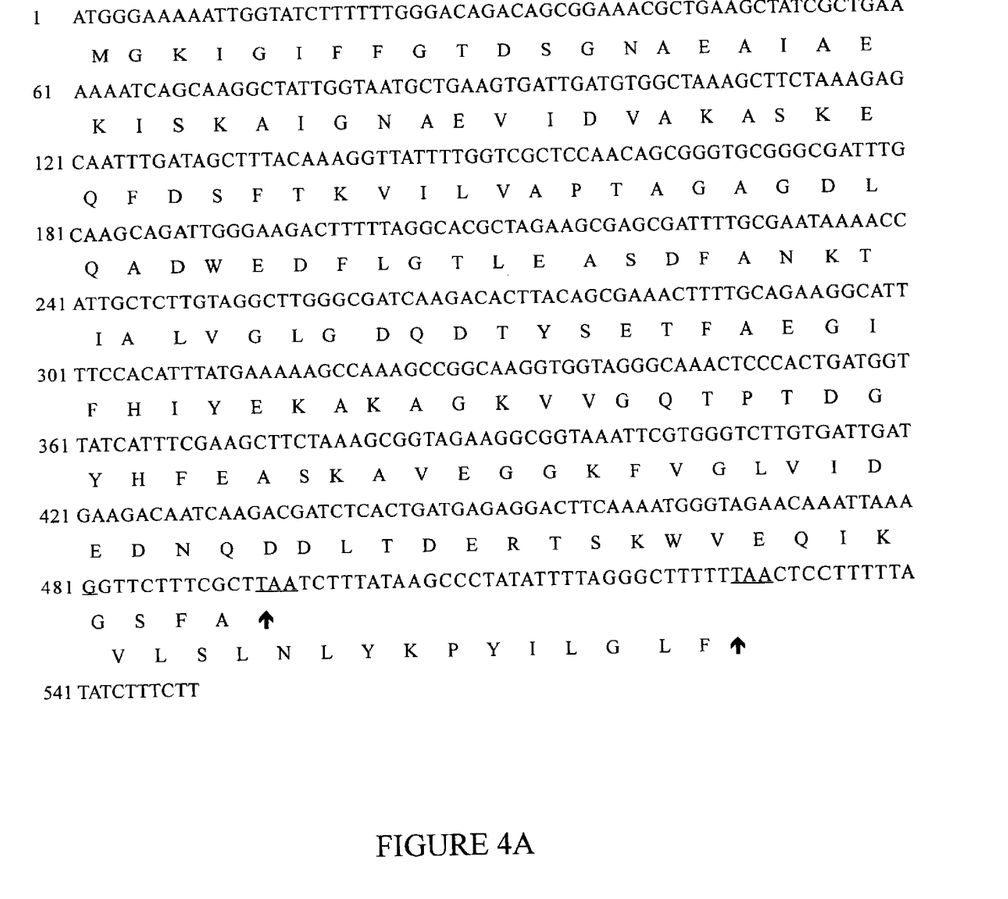
FIG. 4A shows SEQ ID NO:19, the fill-length sequence of the fldA gene of a strain from a patient with MALToma. The underlined G at position 481 of the fldA gene was found more frequently in strains associates with MALToma. The first arrow indicates the stop codon for strains with a G insertion and the second arrow the stop codon for all other strains without a G insertion.

More preferably, said fldA gene has a sequence listing defined in FIG. 4A.

BRIEF DESCRIPTION OF THE DRAWINGS

FIG. 4B shows *H. pylori* FldA amino acid sequence (SEQ ID NO:21) alignment with *E. coli* (SEQ ID NO:22; *E. coli*; accession no. M59426), *E. agglomerans* (SEQ ID NO:23;

Eaggl: GenBank accession no. M38221), Synechococus sp. (SEQ ID NO:24; Synec; GenBank accession no. M88253), *R. capsulatus* (SEQ ID NO:25; Rcaps; GenBank accession no. L44290), *K. pneumoniae* (SEQ ID NO:26; Kpneu; GenBank accession no. X30214), *A variabilis* (SEQ ID NO:27; Avari; GenBank accession no. X14577) and *A. nidulans* (SEQ ID NO:28; Anidu; GenBank accession no. M19116) flavodoxins. A dark background indicates the identical residue homology, and the lighter background shows similar residues. Dots indicate gaps introduced to maximize alignment.

DETAIL DESCRIPTION OF THE INVENTION

Gastric MALToma arises in the mucosa-associated lymphoid tissue acquired as a result of *H. pylori* infection, and the organism can be found in the gastric mucosa in nearly all cases (Hussell, T. et. al., *Lancet,* 1993, 342:571–574). Furthermore, eradication of *H. pylori* from patients with low-grade primary gastric B cell MALToma results in tumor regression, suggesting that this tumor depend on the stimulation from *H. pylori* for growth.

In our study, the truncation of FldA was found in all strains from patients with MALToma and in only 25% of strains from patients with other diseases. The results suggested that the truncated FldA could be specifically associated with gastric MALToma. However, a previous study has shown that when *H. pylori* strains were added to the cultured cells of low-grade gastric lymphomas, substantial proliferative responses were only found to a single *H. pylori* strain in each lymphoma (including a cytotoxin-negative strain) (Wotherspoon, A. C. et. al., *Lancet,* 1991, 338:1175–1176). If the growth of MALToma in vivo is the same as in the in vitro proliferation assay, more than one antigen could be involved in the pathogenesis of MALToma of the stomach.

It has been shown the presence of cagA and the variation of signal sequence in vacA significantly related to its clinical outcome in western countries (Covacci A. et. al., *Proc. Natl. Acad. Sci. USA,* 1993, 90:5791–5795; Atherton J. C. et. al., *Gastroenterology,* 1997, 112:92–97). However, such genetic differences do not seem to exist in Asia, including Taiwan (Covacci A. et. al., *Proc. Natl. Acad. Sci. USA,* 1993, 90:5791–5795; Ito, Y. et. al., *J. Clin. Microbiol.,* 1997, 35:1710–1714). We failed to observe a difference of cagA or vacA in our strains. Therefore, the difference of virulence between these strains was probably caused by factors other than VacA.

The amino acid sequences in FldA of *H. pylori* showed 66%–75% similarities compared with flavodoxins in other species. FldA is usually a cytoplasmic protein in other bacteria. However, the presence of FldA in culture supernatant and its amount were adequate for peptide sequencing in *H. pylori*. This implicated significant amount of FldA was secreted to the extracellular space. The frame of fldA sequences in our strains from patients with MALToma was the same as that of the strain 26695 (Tomb J. F. et. al., *Nature,* 1997, 388:539–547); nevertheless we defined it as an insertion because most strains from patients without MALToma do not have this nucleotide. The insertion of a nucleotide G at position 481 of fldA in *H. pylori* caused a frame shift mutation and a difference in 11 amino acids in the C terminus of this protein. No well-known motif seems to have been changed by this truncation.

Although the biological function of FldA in *H. pylori* is not well understood, our results showed that this mutation significantly changed its antigenicity in patients, as evidenced by the increase of antibody response in patients with gastric MALToma. A short truncation at the C terminus could affect the protein conformation and thus affect its secretion or antigenicity. This antigen might therefore serve as a serological marker for gastric MALToma. This result may also have implications in the pathogenesis of *H. pylori*-associated MALToma of the stomach. In conclusion, a frame shift mutation at position 481 of fldA gene was observed more frequently in *H. pylori* strains associated with gastric MALToma. Antibody to the recombinant FldA protein is more prevalent in patients with MALToma and it may serve as a serological marker for this neoplasm.

Preparation of the Invention and its Application (1) Bacterial Strains and Sera

Figure 1:
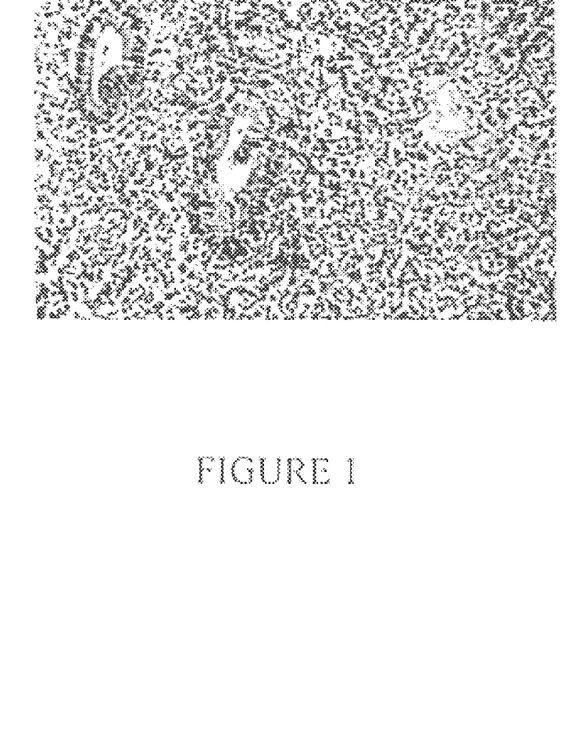
FIG. 1 shows Histopathologic features of low-grade gastric MALToma. Monotonous small to medium-sized lymphoid cells with moderately abundant cytoplasm and angulated nuclei (so-called centrocyte-like cells) infiltrate in the lamina propria. The lymphoid cells also destruct the gastric glands to produce characteristic lymphoepithelial lesions (arrowheads) (H&E; original magnification 1003).
Figure 2:
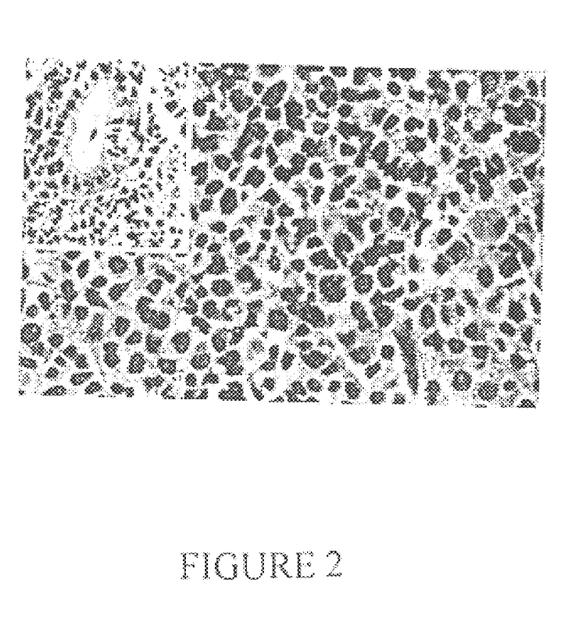
FIG. 2 shows the sheet of large cell infiltration (H&E, original magnification 6003) and characteristic low-grade MALToma features (insert, centrocyte-like cells and lymphoepithelial lesions; H&E, 2003) is diagnostic for high-grade gastric MALToma.

Beginning from 1996, a nationwide cooperative study for gastric MALToma was performed at 8 medical centers in Taiwan. The diagnosis of gastric MALToma was established by histological examination of endoscopic biopsy specimen. The characteristic features of low-grade gastric MALT lymphoma include diffuse infiltration of small to medium-sized centrocyte-like cells in the lamina propria with the presence of lymphoepi-thelial lesions (FIG. 1). If clusters or sheets of transformed blast cells were found within the predominantly low-grade centrocyte-like cell infiltrate or a predominance of large cell infiltrate with only small residual low-grade foci and/or with lymphoepithelial lesions was seen, high-grade MALToma was diagnosed (FIG. 2). Initial diagnosis was made at each medical center and reconfirmed by senior pathologists at the National Taiwan University Hospital and the National Cheng Kung University Hospital.

*H. pylori* strains were isolated from patients with MALToma and other diseases (including chronic gastritis, peptic ulcer, and adenocarcinoma of the stomach) using gastric specimens obtained during endoscopic examinations. During the present study, a total of 17 patients were diagnosed with MALToma (13 patients with low-grade MALToma and 4 patients with high-grade MALToma). Serum samples from these patients were collected before *H. pylori* treatment. However, only 9 *H. pylori* strains were isolated from the 17 patients. All the strains and sera from the present cooperative study for MALToma were tested. Beginning from 1990, we isolated approximately 600 *H. pylori* strains from patients undergoing endoscopic examinations at the National Taiwan University Hospital. Their paired sera were obtained at the same time. Serum samples collected from 42 patients (14 patients with duodenal ulcer, 14 patients with gastric cancer, and 14 patients with gastritis) and *H. pylori* strains from 17 patients were randomly selected as the control (Wang J. T. et. al., *J. Infect. Dis.,* 1993, 168:1544–1548; Lin J. T. et. al., *Eur. J. Cancer,* 1995, 31A:1879–1882).

(2) Protein Preparation and Western Blot Analysis

Serum-free proteins were obtained by growing bacteria in Brucella broth containing 0.2% b-cyclodextrin without serum supplement (Wang J. T. et. al., *J. Microbiol. Immunol. Infect.,* 1998, 31:146–150). Membrane proteins were extracted using a previously described method (Kantke K., *Mol. Gen. Genet.*, 1981, 182:288–292). Secreted proteins were obtained from culture supernatant. Bacterial proteins were run in an 8%–12% sodium dodecyl sulfate-polyacrylamide gel electrophoresis (SDS-PAGE).

Western blots were then performed using sera from 17 patients with MALToma before treatment for *H. pylori*. Posttreatment sera were tested in 6 patients in whom *H. pylori* eradication was documented and who were followed up for 1 year. The sera were subjected to 1:500 to 1:1000 dilution as the primary antibody and detected by an enhanced chemiluminescence Western blotting kit (Amersham, Little Chalfont, Bucks, England). Running bacterial proteins in parallel was done to identify significant differences between strains from MALToma and other diseases.

3) Purification of Protein Secreted into the Medium and Amino Acid Sequencing

The supernatant of *H. pylori* culture was concentrated sixfold by Centricon tubes (Amicon, Danvers, Mass.) and then dialyzed against 20 mol/L HEPES (pH 7.6), 0.1 mmol/L EDTA, 10% glycerol, 0.5 mmol/L dithriothreitol, and 1 mmol/L phenylmethylsulfonyl fluoride. The proteins were further purified by ion exchange chromatography. The protein fractions were then eluted stepwise with a buffer (20 mmol/L HEPES [pH 7.6], 0.1 mmol/L EDTA, 10% glycerol, 0.5 mmol/L dithriothreitol, and 1 mmol/L phenylmethylsulfonyl fluoride) containing 50 mmol/L KCl, 100 mmol/L KCl, 150 mmol/L KCl, or 200 mmol/L KCl. After electrophoresis, the protein was electrotransferred to a polyvinylidene difluoride membrane using a Fast-Blot semi-dry chamber (Biometra, Gottingen, Germany) in 10 mmol/L 3-[cyclohexylamino]-2-hydroxy-1-propanesulfonic acid (pH 10.5), 0.05% dithiothreitol, and 15% methanol. The target protein was confirmed by Western blot using high-titer serum with 1:500 dilution and visualized by Coomassie blue staining.

Figure 3:
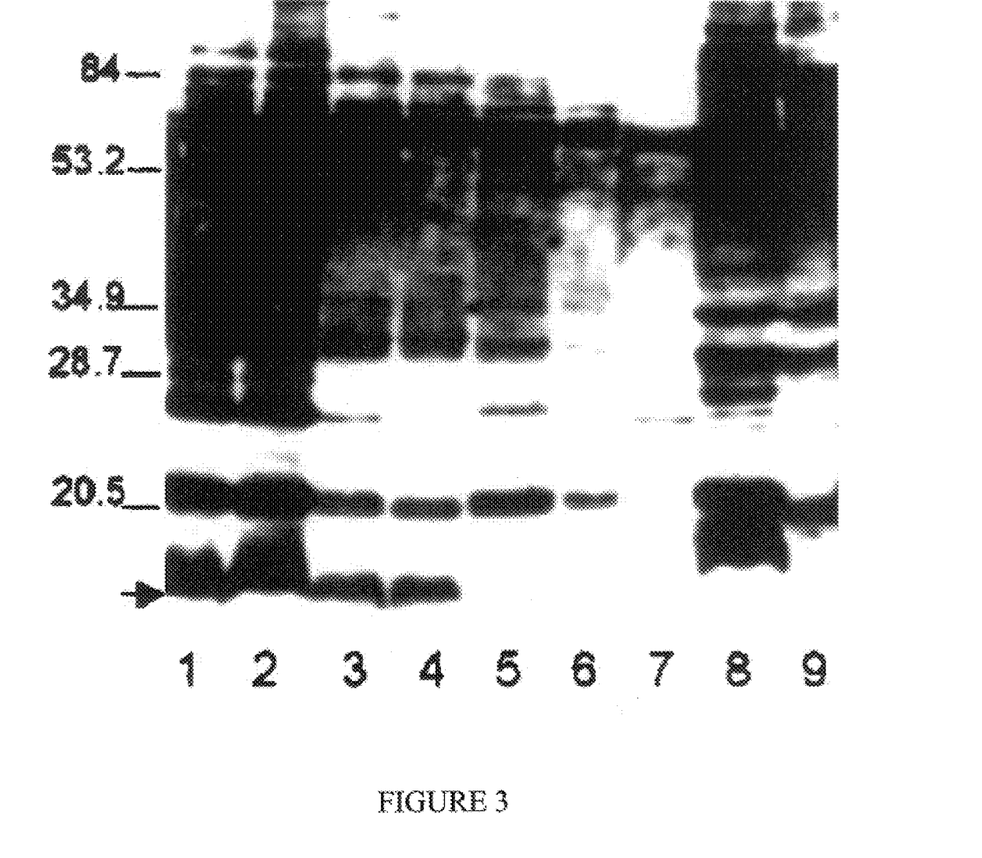
FIG. 3. shows a 19-kilodalton antigen was seen in strains isolated from patients with MALToma by Western blot using sera from patients with MALToma. Lanes 1–4, secreted proteins of *H. pylori* extracted from patients with MALToma. Lanes 5–9, Secreted proteins of *H. pylori* extracted from patients with other diseases. Arrow indicates 19 kilodaltons.

No significant difference was found in membranous protein by this assay; however, a 19-kilodalton secreted protein of *H. pylori* was constantly noted in the strains from MALToma patients but uncommonly in strains from patients with other diseases (FIG. 3). This protein was purified by ion exchange chromatography, and the amino acid sequences were determined by Edman's degradation method. The 19 N-terminal amino acids of the protein were K I G I F F G T D S G N A E A I A E K (SEQ ID NO:1). Comparison of the amino acid sequence revealed a 92% homology to open reading frames HP1161, fldA, of the genome of strain 26695 (Tomb J. F. et. al., *Nature*, 1997, 388:539–54). The fldA gene encodes a flavodoxin protein in Synechococus species.

4) Polymerase Chain Reaction and DNA Sequencing

After peptide sequencing, polymerase chain reaction (PCR) was performed to clone the candidate gene using conditions described previously (Lin J. T. et. al., *Eur. J. Cancer*, 1995, 31A: 1879–1882) by using sequences derived from the published sequences of strain 26695 as primer pairs (sense, 5' ACA CAA GGA TCC GAT ATG GGA AAA (SEQ ID NO:3); antisense, 5' TTT AGG GCC CAT AAA AAA TTA AGC) (Tomb J. F. et. al., *Nature*, 1997, 388:539–547). Coding sequences of the fldA gene of a patient with MALToma (patient 1, Table 1) were amplified. DNA sequences were determined in PCR products and in clones in a plasmid vector, pCR2.1-TOPO (Invitrogen, Carlsbad, Calif.). Sequencing reactions were performed on an ABI 373 automated sequencer (ABI, Foster City, Calif.) as described previously (Chang K.C. et. al., *Biochem. Biophys. Res. Commun.*, 1997, 236:785–788). PCR and direct sequencing were performed at least twice to determine DNA sequences for each strain.

Figure 4B:
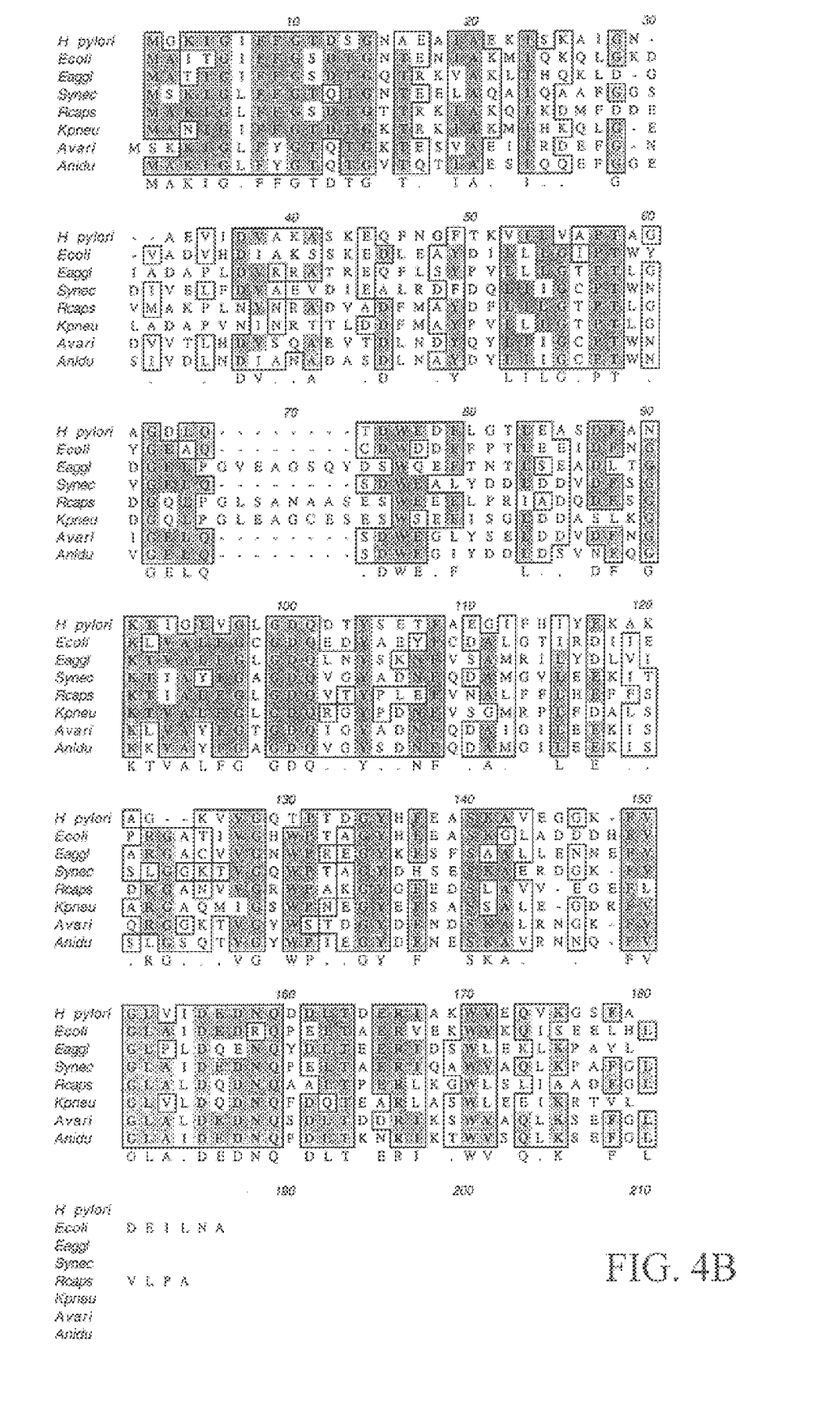

Nucleotide sequences of the fldA gene were determined in 26 clinical isolates (all 9 isolates from patients with MALToma and 17 from patients with other diseases). Comparison of the nucleotide sequence of the fldA gene revealed that a nucleotide G insertion at position 481 of the gene was more frequently observed in strains associated with MALToma than in strains not associated with MALToma (9 of 9 vs. 6 of 17; P 0.002). The insertion caused a frame shift mutation and a truncation of 11 amino acids at the C terminus (FIG. 4A). Sequences in strains without a G insertion showed a second stop codon at nucleotide 527. The amino acid sequences of the FldA revealed putative motifs including N-glycosylation site (78–81 NKTI (SEQ ID NO:4)), casein kinase II phosphorylation site (62–65 TDWE (SEQ ID NO:5); 91–94 TYSE (SEQ ID NO:6); 95–98 TFAE (SEQ ID NO:7); 116–119 TPTD (SEQ ID NO:8), N-myristoylation site (5–10 GIFFGT (SEQ ID NO:9); 9–14 GTDSGN (SEQ ID NO:10); 13–18 GNAEAI (SEQ ID NO:11); 69–74 GTLEAS (SEQ ID NO:12); 114–119 GQTPTD (SEQ ID NO:13), and a "helix-loop-helix" dimerization domain signature (46–54 TKVILVAPT (SEQ ID NO:14)). No well-known motif was found at the C-terminal end. Comparison of the FldA sequences with flavodoxins in other species, including *E. coli, Enterobacter agglomerans,* Synechococcus sp., *Rhodobacter capsulatus, Klebsiella pneumoniae, Anabaena variabilis,* and *Anacystis nidulans,* revealed 66%–75% similarities (FIG. 4B).

5) Detection of cagA and vacA Gene

The presence of cytotoxin-associated gene A (cagA) and vacuolating cytotoxin A gene (vacA) has been reported to be associated with the clinical outcomes (Covacci A. et. al., *Proc. Natl. Acad. Sci. USA*, 1993, 90:5791–5795; Atherton J. C. et. al., *Gastroenterology*, 1997, 112:92–97). Therefore, we studied the cagA and vacA genes to explore whether an association of these two genes and MALToma exists. The presence cagA and vacA were detected in 26 *H. pylori* strains by PCR (Yang J. C. et. al., *Am. J. Gastroenterol.*, 1997, 92:1316–1321). PCR primers for vacA fragment amplification are 5' CCA TAT TGA CTC GTT CGC CAA ACGC 3'(SEQ ID NO:15) (Vf1) and 5' CCT AAA TGG TTA TAG CTC ACG CCC 3'(SEQ ID NO:22) (Vr1); and 5' GAT AAC AGG CAA GCT TTT GAGG 3'(SEQ ID NO:18) (Cf1) and 5' CTG CAA AAG ATT GTT TGC GAGA 3' (Cr1) for cagA fragment.

cagA and vacA were characterized in 26 *H. pylori* isolates by PCR. Of the 9 strains from patients with MALToma, all were positive for vacA and 6 isolates were positive for cagA. All 17 isolates from other gastrointestinal diseases were positive for both cagA and vacA.

6) Expression of the fldA Gene and Antibody Response in Serum Samples

Coding sequences of the fldA gene from a strain with MALToma were cloned into a pGEX-2T vector (Pharmacia, Hong Kong) by a recombinant PCR (primers: sense, 5' ACA CAA GGA TCC GAT ATG GGA AAA (SEQ ID NO:2); antisense, 5' TTT AGG GCC CAT AAA AAA TTA AGC (SEQ ID NO:13)). The protein was expressed in a BL21 *Eschcerichia coli* strain after induction by 0.4 mmol/L isopropyl-D-thiogalactopyranoside (IPTG) and purified by a glutathione S-transferase (GST) affinity column (Pharmacia).

The purified recombinant FldA protein was run in 12% SDS-PAGE. Western blots were then performed using serum samples from all the 17 patients with gastric MALToma and the 42 patients with other gastrointestinal diseases (including 14 with chronic gastritis, 14 with peptic ulcer, and 14 with adenocarcinoma of the stomach). The serum samples were subjected to 1:500 dilution as the primary antibody and detected by an enhanced chemiluminescence Western blotting Kit (Amersham).

Figure 5A:
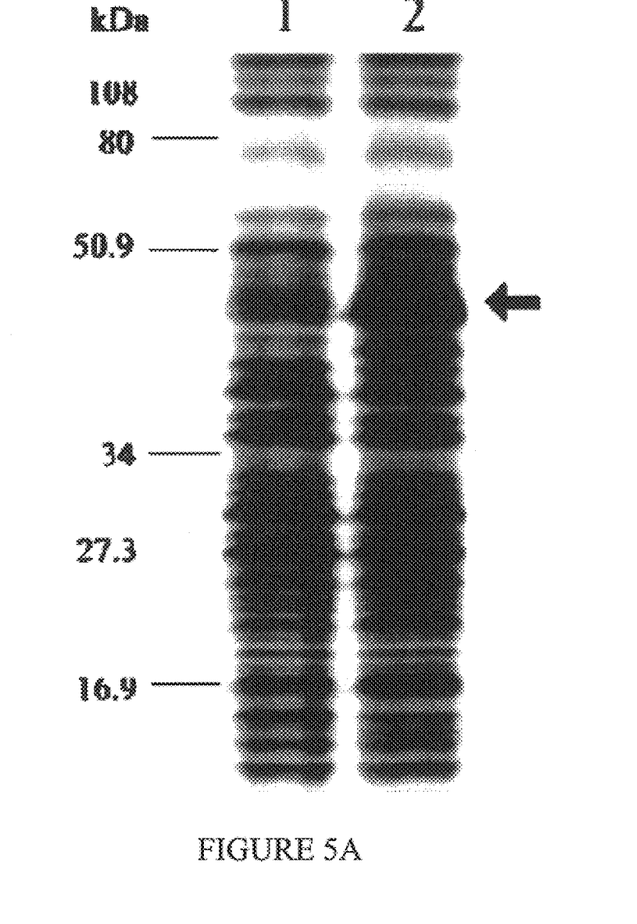
FIG. 5A shows Coomassie blue staining bacterial protein extracts of a BL21 *E. coli* strain containing a pGEX-2T vector and the fldA insert. Lane 1, without IPTG treatment; lane 2, 2 hours after 0.4 mmol/L IPTG induction. Arrow indicates 45 kilodaltons, expected size of the recombinant GST-FldA fusion protein.
Figure 5B:
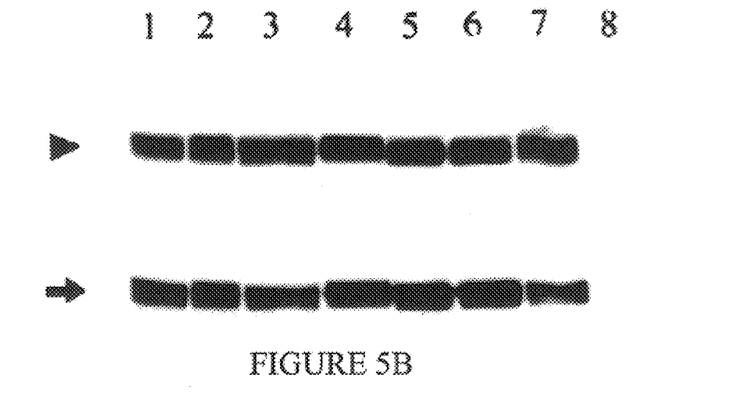
FIG. 5B shows Western blot analysis using the recombinant FldA protein as antigen and sera of patients with gastric MALToma as an antibody. Results of 8 patients. Seven patients are positive (lanes 1–7) and one is negative (lane 8) for antibody to recombinant FldA. Arrowhead indicates 45 kilodaltons, the GST-FldA fusion protein. Arrow indicates 19 kilodaltons, the FldA protein.

In 17 patients with MALToma, 12 were positive for antibody to the recombinant FldA protein; 7 of 42 patients with other diseases were positive (12 of 17 vs. 7 of 42; P 0.0001) (FIG. 5B). None of the serum samples reacted with GST alone (data not shown). There was no significant difference in age and sex between these two groups (Table 2). All 6 patients who were seropositive before treatment remained positive for anti-FldA in serum samples 12–18 months after H. pylori eradication treatment. Antibody titers decreased in 2 of the 6 patients after treatment, and 4 remained the same. There seemed to be no difference between seropositive and seronegative patients with MALToma in the histological grade, staging, or clinical course (Table 1).

TABLE 1

Results of 17 Patients With MALToma Tested for Antibody to Recombinant FldA#.

| Patients | Sex | Age (yr) | Antibody to FldA |
| --- | --- | --- | --- |
| 1* | F | 56 | Positive |
| 2 | M | 74 | Positive |
| 3* | F | 68 | Positive |
| 4* | M | 71 | Positive |
| 5* | F | 84 | Negative |
| 6 | F | 47 | Positive |
| 7 | F | 72 | Negative |
| 8* | M | 44 | Positive |
| 9* | M | 43 | Negative |
| 10 | M | 68 | Positive |
| 11* | F | 71 | Positive |

TABLE 1-continued

Results of 17 Patients With MALToma Tested for Antibody to Recombinant FldA#.

| Patients | Sex | Age (yr) | Antibody to FldA |
| --- | --- | --- | --- |
| 12* | F | 67 | Positive |
| 13 | M | 46 | Negative |
| 14 | F | 43 | Negative |
| 15* | F | 68 | Positive |
| 16 | F | 64 | Positive |
| 17 | F | 54 | Positive |

NOTE. Patients 1–13 are classified with low-grade histology grading, patients 14–17 with high-grade histology grading. Patients 1 and 9 are staged as IIE-1, and the other 15 patients as stage I.
*The "G" insertion at fldA was detected in H. pylori strain.

TABLE 2

Antibody to the Recombinant FldA Protein of H. pylori.

| | MALToma patients (n = 17) | Other patients (n = 42) | P value |
| --- | --- | --- | --- |
| Sex (M/F) | 8/9 | 19/23 | NS[a] |
| Mean age, yr | 62.3 | 56.9 | NS[b] |
| (range) | (43–84) | (30–75) | |
| Antibody to FldA (positive/total) | 12/17 (70.6%) | 7/42 (16.7%) | 0.0001[a] |

[a]Chi-square test.
[b]Student' t test.

What is claimed is:

1. A method of using a putative flavodoxin gene (fldA) from *Helicobacter pylori* to screen Taiwanese patients infected with *Helicobacter pylori* for those that are in a high risk of developing mucosa-associated lymphoid tissue lymphoma of the stomach (MALToma), the method comprising using a molecular biology technique to detect the expression of fldA gene of *Helicobacter pylori* from the Taiwanese patients so that a guanidine insertion at a position of 481 of SEQ ID NO:19 can be determined, whereby the presence of the guanidine insertion indicates the high risk of developing MALToma.

2. The method according to claim 1, wherein said fldA gene has a sequence listing defined in FIG. 4A.

3. The method according to claim 1, wherein said molecular biology technique is DNA sequencing, DNA probe, gene chip, RT-PCR, or Southern hybridization.

* * * * *

SEQUENCE LISTING

<160> NUMBER OF SEQ ID NOS: 31

<210> SEQ ID NO 1
<211> LENGTH: 19
<212> TYPE: PRT
<213> ORGANISM: Helicobacter pylori

<400> SEQUENCE: 1

Lys Ile Gly Ile Phe Phe Gly Thr Asp Ser Gly Asn Ala Glu Ala Ile
 1               5                   10                  15

Ala Glu Lys

<210> SEQ ID NO 2
<211> LENGTH: 24
<212> TYPE: DNA
<213> ORGANISM: Helicobacter pylori

<400> SEQUENCE: 2
acacaaggat ccgatatggg aaaa                                    24

<210> SEQ ID NO 3
<211> LENGTH: 24
<212> TYPE: DNA
<213> ORGANISM: Helicobacter pylori

<400> SEQUENCE: 3
tttagggccc ataaaaaatt aagc                                    24

<210> SEQ ID NO 4
<211> LENGTH: 4
<212> TYPE: PRT
<213> ORGANISM: Helicobacter pylori

<400> SEQUENCE: 4

Asn Lys Thr Ile
 1

<210> SEQ ID NO 5
<211> LENGTH: 4
<212> TYPE: PRT
<213> ORGANISM: Helicobacter pylori

<400> SEQUENCE: 5

Thr Asp Trp Glu
 1

<210> SEQ ID NO 6
<211> LENGTH: 4
<212> TYPE: PRT
<213> ORGANISM: Helicobacter pylori

<400> SEQUENCE: 6

Thr Tyr Ser Glu
 1

<210> SEQ ID NO 7
<211> LENGTH: 4
<212> TYPE: PRT
<213> ORGANISM: Helicobacter pylori

<400> SEQUENCE: 7

Thr Phe Ala Glu
 1

<210> SEQ ID NO 8
<211> LENGTH: 4
<212> TYPE: PRT
<213> ORGANISM: Helicobacter pylori

<400> SEQUENCE: 8

Thr Pro Thr Asp
 1

<210> SEQ ID NO 9
<211> LENGTH: 6
<212> TYPE: PRT
<213> ORGANISM: Helicobacter pylori

<400> SEQUENCE: 9

Gly Ile Phe Phe Gly Thr
 1               5

<210> SEQ ID NO 10
<211> LENGTH: 6
<212> TYPE: PRT
<213> ORGANISM: Helicobacter pylori

<400> SEQUENCE: 10

Gly Thr Asp Ser Gly Asn
 1               5

```
<210> SEQ ID NO 11
<211> LENGTH: 6
<212> TYPE: PRT
<213> ORGANISM: Helicobacter pylori

<400> SEQUENCE: 11

Gly Asn Ala Glu Ala Ile
 1               5

<210> SEQ ID NO 12
<211> LENGTH: 6
<212> TYPE: PRT
<213> ORGANISM: Helicobacter pylori

<400> SEQUENCE: 12

Gly Thr Leu Glu Ala Ser
 1               5

<210> SEQ ID NO 13
<211> LENGTH: 6
<212> TYPE: PRT
<213> ORGANISM: Helicobacter pylori

<400> SEQUENCE: 13

Gly Gln Thr Pro Thr Asp
 1               5

<210> SEQ ID NO 14
<211> LENGTH: 9
<212> TYPE: PRT
<213> ORGANISM: Helicobacter pylori

<400> SEQUENCE: 14

Thr Lys Val Ile Leu Val Ala Pro Thr
 1               5

<210> SEQ ID NO 15
<211> LENGTH: 25
<212> TYPE: DNA
<213> ORGANISM: Helicobacter pylori

<400> SEQUENCE: 15
ccatattgac tcgttcgcca aacgc                                    25

<210> SEQ ID NO 16
<211> LENGTH: 24
<212> TYPE: DNA
<213> ORGANISM: Helicobacter pylori

<400> SEQUENCE: 16
cctaaatggt tatagctcac gccc                                     24

<210> SEQ ID NO 17
<211> LENGTH: 22
<212> TYPE: DNA
<213> ORGANISM: Helicobacter pylori

<400> SEQUENCE: 17
gataacaggc aagcttttga gg                                       22

<210> SEQ ID NO 18
<211> LENGTH: 22
<212> TYPE: DNA
<213> ORGANISM: Helicobacter pylori
```

-continued

<400> SEQUENCE: 18
ctgcaaaaga ttgtttgcga ga                                                  22

<210> SEQ ID NO 19
<211> LENGTH: 549
<212> TYPE: DNA
<213> ORGANISM: Helicobacter pylori

<400> SEQUENCE: 19

| atg | gga | aaa | att | ggt | atc | ttt | ttt | ggg | aca | gac | agc | gga | aac | gct | gaa | 48 |
| Met | Gly | Lys | Ile | Gly | Ile | Phe | Phe | Gly | Thr | Asp | Ser | Gly | Asn | Ala | Glu | |
| 1 | | | | 5 | | | | | 10 | | | | | 15 | | |

| gct | atc | gct | gaa | aaa | atc | agc | aag | gct | att | ggt | aat | gct | gaa | gtg | att | 96 |
| Ala | Ile | Ala | Glu | Lys | Ile | Ser | Lys | Ala | Ile | Gly | Asn | Ala | Glu | Val | Ile | |
| | | | 20 | | | | | 25 | | | | | 30 | | | |

| gat | gtg | gct | aaa | gct | tct | aaa | gag | caa | ttt | gat | agc | ttt | aca | aag | gtt | 144 |
| Asp | Val | Ala | Lys | Ala | Ser | Lys | Glu | Gln | Phe | Asp | Ser | Phe | Thr | Lys | Val | |
| | | 35 | | | | | 40 | | | | | 45 | | | | |

| att | ttg | gtc | gct | cca | aca | gcg | ggt | gcg | ggc | gat | ttg | caa | gca | gat | tgg | 192 |
| Ile | Leu | Val | Ala | Pro | Thr | Ala | Gly | Ala | Gly | Asp | Leu | Gln | Ala | Asp | Trp | |
| 50 | | | | | 55 | | | | | 60 | | | | | | |

| gaa | gac | ttt | tta | ggc | acg | cta | gaa | gcg | agc | gat | ttt | gcg | aat | aaa | acc | 240 |
| Glu | Asp | Phe | Leu | Gly | Thr | Leu | Glu | Ala | Ser | Asp | Phe | Ala | Asn | Lys | Thr | |
| 65 | | | | 70 | | | | | 75 | | | | | 80 | | |

| att | gct | ctt | gta | ggc | ttg | ggc | gat | caa | gac | act | tac | agc | gaa | act | ttt | 288 |
| Ile | Ala | Leu | Val | Gly | Leu | Gly | Asp | Gln | Asp | Thr | Tyr | Ser | Glu | Thr | Phe | |
| | | | | 85 | | | | | 90 | | | | | 95 | | |

| gca | gaa | ggc | att | ttc | cac | att | tat | gaa | aaa | gcc | aaa | gcc | ggc | aag | gtg | 336 |
| Ala | Glu | Gly | Ile | Phe | His | Ile | Tyr | Glu | Lys | Ala | Lys | Ala | Gly | Lys | Val | |
| | | | 100 | | | | | 105 | | | | | 110 | | | |

| gta | ggg | caa | act | ccc | act | gat | ggt | tat | cat | ttc | gaa | gct | tct | aaa | gcg | 384 |
| Val | Gly | Gln | Thr | Pro | Thr | Asp | Gly | Tyr | His | Phe | Glu | Ala | Ser | Lys | Ala | |
| | 115 | | | | | 120 | | | | | 125 | | | | | |

| gta | gaa | ggc | ggt | aaa | ttc | gtg | ggt | ctt | gtg | att | gat | gaa | gac | aat | caa | 432 |
| Val | Glu | Gly | Gly | Lys | Phe | Val | Gly | Leu | Val | Ile | Asp | Glu | Asp | Asn | Gln | |
| 130 | | | | | 135 | | | | | 140 | | | | | | |

| gac | gat | ctc | act | gat | gag | agg | act | tca | aaa | tgg | gta | gaa | caa | att | aaa | 480 |
| Asp | Asp | Leu | Thr | Asp | Glu | Arg | Thr | Ser | Lys | Trp | Val | Glu | Gln | Ile | Lys | |
| 145 | | | | 150 | | | | | 155 | | | | | 160 | | |

| ggt | tct | ttc | gct | taatctttat | aagccctata | ttttagggct | tttttaactc | | | | | | | | | 532 |
| Gly | Ser | Phe | Ala | | | | | | | | | | | | | | cttttatat ctttctt                                                         549

<210> SEQ ID NO 20
<211> LENGTH: 164
<212> TYPE: PRT
<213> ORGANISM: Helicobacter pylori

<400> SEQUENCE: 20

| Met | Gly | Lys | Ile | Gly | Ile | Phe | Phe | Gly | Thr | Asp | Ser | Gly | Asn | Ala | Glu |
| 1 | | | | 5 | | | | | 10 | | | | | 15 | |

| Ala | Ile | Ala | Glu | Lys | Ile | Ser | Lys | Ala | Ile | Gly | Asn | Ala | Glu | Val | Ile |
| | | | 20 | | | | | 25 | | | | | 30 | | |

| Asp | Val | Ala | Lys | Ala | Ser | Lys | Glu | Gln | Phe | Asp | Ser | Phe | Thr | Lys | Val |
| | | 35 | | | | | 40 | | | | | 45 | | | |

| Ile | Leu | Val | Ala | Pro | Thr | Ala | Gly | Ala | Gly | Asp | Leu | Gln | Thr | Asp | Trp |
| 50 | | | | | 55 | | | | | 60 | | | | | |

| Glu | Asp | Phe | Leu | Gly | Thr | Leu | Glu | Ala | Ser | Asp | Phe | Ala | Asn | Lys | Thr |
| 65 | | | | 70 | | | | | 75 | | | | | 80 | |

```
Ile Ala Leu Val Gly Leu Gly Asp Gln Asp Thr Tyr Ser Glu Thr Phe
                85                  90                  95

Ala Glu Gly Ile Phe His Ile Tyr Glu Lys Ala Lys Ala Gly Lys Val
            100                 105                 110

Val Gly Gln Thr Pro Thr Asp Gly Tyr His Phe Glu Ala Ser Lys Ala
            115                 120                 125

Val Glu Gly Gly Lys Phe Val Gly Leu Val Ile Asp Glu Asp Asn Gln
            130                 135                 140

Asp Asp Leu Thr Asp Glu Arg Thr Ser Lys Trp Val Glu Gln Ile Lys
145                 150                 155                 160

Gly Ser Phe Ala

<210> SEQ ID NO 21
<211> LENGTH: 164
<212> TYPE: PRT
<213> ORGANISM: Helicobacter pylori

<400> SEQUENCE: 21

Met Gly Lys Ile Gly Ile Phe Phe Gly Thr Asp Ser Gly Asn Ala Glu
 1               5                  10                  15

Ala Ile Ala Glu Lys Ile Ser Lys Ala Ile Gly Asn Ala Glu Val Ile
            20                  25                  30

Asp Val Ala Lys Ala Ser Lys Glu Gln Phe Asn Gly Phe Thr Lys Val
            35                  40                  45

Ile Leu Val Ala Pro Thr Ala Gly Ala Gly Asp Leu Gln Ala Asp Trp
        50                  55                  60

Glu Asp Phe Leu Gly Thr Leu Glu Ala Ser Asp Phe Ala Asn Lys Thr
65                  70                  75                  80

Ile Gly Leu Val Gly Leu Gly Asp Gln Asp Thr Tyr Ser Glu Thr Phe
                85                  90                  95

Ala Glu Gly Ile Phe His Ile Tyr Glu Lys Ala Lys Ala Gly Lys Val
            100                 105                 110

Val Gly Gln Thr Pro Thr Asp Gly Tyr His Phe Glu Ala Ser Lys Ala
            115                 120                 125

Val Glu Gly Gly Lys Phe Val Gly Leu Val Ile Asp Glu Asp Asn Gln
            130                 135                 140

Asp Asp Leu Thr Asp Glu Arg Ile Ala Lys Trp Val Glu Gln Val Lys
145                 150                 155                 160

Gly Ser Phe Ala

<210> SEQ ID NO 22
<211> LENGTH: 176
<212> TYPE: PRT
<213> ORGANISM: E. coli

<400> SEQUENCE: 22

Met Ala Ile Thr Gly Ile Phe Phe Gly Ser Asp Thr Gly Asn Thr Glu
 1               5                  10                  15

Asn Ile Ala Lys Met Ile Gln Lys Gln Leu Gly Lys Asp Val Ala Asp
            20                  25                  30

Val His Asp Ile Ala Lys Ser Ser Lys Glu Asp Leu Glu Ala Tyr Asp
            35                  40                  45

Ile Leu Leu Leu Gly Ile Pro Thr Trp Tyr Tyr Gly Glu Ala Gln Cys
        50                  55                  60

Asp Trp Asp Asp Phe Phe Pro Thr Leu Glu Glu Ile Asp Phe Asn Gly
```

```
                65                  70                  75                  80
Lys Leu Val Ala Leu Phe Gly Cys Gly Asp Gln Glu Asp Tyr Ala Glu
                    85                  90                  95

Tyr Phe Cys Asp Ala Leu Gly Thr Ile Arg Asp Ile Ile Glu Pro Arg
                100                 105                 110

Gly Ala Thr Ile Val Gly His Trp Pro Thr Ala Gly Tyr His Phe Glu
                115                 120                 125

Ala Ser Lys Gly Leu Ala Asp Asp His Phe Val Gly Leu Ala Ile
                130                 135                 140

Asp Glu Asp Arg Gln Pro Glu Leu Thr Ala Glu Arg Val Glu Lys Trp
145                 150                 155                 160

Val Lys Gln Ile Ser Glu Glu Leu His Leu Asp Glu Ile Leu Asn Ala
                165                 170                 175

<210> SEQ ID NO 23
<211> LENGTH: 177
<212> TYPE: PRT
<213> ORGANISM: E. agglomerans

<400> SEQUENCE: 23

Met Ala Thr Ile Gly Ile Phe Phe Gly Ser Asp Thr Gly Gln Thr Arg
  1               5                  10                  15

Lys Val Ala Lys Leu Ile His Gln Lys Leu Asp Gly Ile Ala Asp Ala
                 20                  25                  30

Pro Leu Asp Val Arg Arg Ala Thr Arg Glu Gln Phe Leu Ser Tyr Pro
             35                  40                  45

Val Leu Leu Leu Gly Thr Pro Thr Leu Gly Asp Gly Glu Leu Pro Gly
         50                  55                  60

Val Glu Ala Gly Ser Gln Tyr Asp Ser Trp Gln Glu Phe Thr Asn Thr
 65                  70                  75                  80

Leu Ser Glu Ala Asp Leu Thr Gly Lys Thr Val Ala Leu Phe Gly Leu
                 85                  90                  95

Gly Asp Gln Leu Asn Tyr Ser Lys Asn Phe Val Ser Ala Met Arg Ile
                100                 105                 110

Leu Tyr Asp Leu Val Ile Ala Arg Gly Ala Cys Val Val Gly Asn Trp
            115                 120                 125

Pro Arg Glu Gly Tyr Lys Phe Ser Phe Ser Ala Ala Leu Leu Glu Asn
130                 135                 140

Asn Glu Phe Val Gly Leu Pro Leu Asp Gln Glu Asn Gln Tyr Asp Leu
145                 150                 155                 160

Thr Glu Glu Arg Ile Asp Ser Trp Leu Glu Lys Leu Lys Pro Ala Val
                165                 170                 175

Leu

<210> SEQ ID NO 24
<211> LENGTH: 170
<212> TYPE: PRT
<213> ORGANISM: Synechococcus sp.

<400> SEQUENCE: 24

Met Ser Lys Ile Gly Leu Phe Phe Gly Thr Gln Thr Gly Asn Thr Glu
  1               5                  10                  15

Glu Leu Ala Gln Ala Ile Gln Ala Ala Phe Gly Gly Ser Asp Ile Val
                 20                  25                  30

Glu Leu Phe Asp Val Ala Glu Val Asp Ile Glu Ala Leu Arg Asp Phe
             35                  40                  45
```

—continued

```
Asp Gln Leu Ile Ile Gly Cys Pro Thr Trp Asn Val Gly Glu Leu Gln
            50                  55                  60

Ser Asp Trp Glu Ala Leu Tyr Asp Asp Leu Asp Asp Val Asp Phe Ser
 65                  70                  75                  80

Gly Lys Thr Ile Ala Tyr Phe Gly Ala Gly Asp Gln Val Gly Tyr Ala
                    85                  90                  95

Asp Asn Phe Gln Asp Ala Met Gly Val Leu Glu Glu Lys Ile Thr Ser
                    100                 105                 110

Leu Gly Gly Lys Thr Val Gly Gln Trp Pro Thr Ala Gly Tyr Asp His
                    115                 120                 125

Ser Glu Ser Lys Ala Glu Arg Asp Gly Lys Phe Val Gly Leu Ala Ile
            130                 135                 140

Asp Glu Asp Asn Gln Pro Glu Leu Thr Ala Glu Arg Ile Gln Ala Trp
145                 150                 155                 160

Val Ala Gln Leu Lys Pro Ala Phe Gly Leu
                    165                 170

<210> SEQ ID NO 25
<211> LENGTH: 182
<212> TYPE: PRT
<213> ORGANISM: R. capsulatus

<400> SEQUENCE: 25

Met Ala Lys Ile Gly Leu Phe Phe Gly Ser Asp Thr Gly Thr Thr Arg
 1                   5                  10                  15

Lys Ile Ala Lys Gln Ile Lys Asp Met Phe Asp Asp Glu Val Met Ala
                    20                  25                  30

Lys Pro Leu Asn Val Asn Arg Ala Asp Val Ala Asp Phe Met Ala Tyr
                    35                  40                  45

Asp Phe Leu Ile Leu Gly Thr Pro Thr Leu Gly Asp Gly Gln Leu Pro
            50                  55                  60

Gly Leu Ser Ala Asn Ala Ala Ser Glu Ser Trp Glu Glu Phe Leu Pro
 65                  70                  75                  80

Arg Ile Ala Asp Gln Asp Phe Ser Gly Lys Thr Ile Ala Leu Phe Gly
                    85                  90                  95

Leu Gly Asp Gln Val Thr Tyr Pro Leu Glu Phe Val Asn Ala Leu Phe
                    100                 105                 110

Phe Leu His Glu Phe Phe Ser Asp Arg Gly Ala Asn Val Val Gly Arg
            115                 120                 125

Trp Pro Ala Lys Gly Tyr Gly Phe Glu Asp Ser Leu Ala Val Val Glu
130                 135                 140

Gly Glu Phe Leu Gly Leu Ala Leu Asp Gln Asp Asn Gln Ala Ala Leu
145                 150                 155                 160

Thr Pro Glu Arg Leu Lys Gly Trp Leu Ser Leu Ile Ala Ala Asp Phe
                    165                 170                 175

Gly Leu Val Leu Pro Ala
            180

<210> SEQ ID NO 26
<211> LENGTH: 176
<212> TYPE: PRT
<213> ORGANISM: K. pneumoniae

<400> SEQUENCE: 26

Met Ala Asn Ile Gly Ile Phe Phe Gly Thr Asp Thr Gly Lys Thr Arg
 1                   5                  10                  15
```

-continued

Lys Ile Ala Lys Met Ile His Lys Gln Leu Gly Glu Leu Ala Asp Ala
            20                  25                  30

Pro Val Asn Ile Asn Arg Thr Thr Leu Asp Asp Phe Met Ala Tyr Pro
            35                  40                  45

Val Leu Leu Leu Gly Thr Pro Thr Leu Gly Asp Gly Gln Leu Pro Gly
        50                  55                  60

Leu Glu Ala Gly Cys Glu Ser Glu Ser Trp Ser Glu Phe Ile Ser Gly
 65                  70                  75                  80

Leu Asp Asp Ala Ser Leu Lys Gly Lys Thr Val Ala Leu Phe Gly Leu
                85                  90                  95

Gly Asp Gln Arg Gly Tyr Pro Asp Asn Phe Val Ser Gly Met Arg Pro
            100                 105                 110

Leu Phe Asp Ala Leu Ser Ala Arg Gly Ala Gln Met Ile Gly Ser Trp
            115                 120                 125

Pro Asn Glu Gly Tyr Glu Phe Ser Ala Ser Ser Ala Leu Glu Gly Asp
            130                 135                 140

Arg Phe Val Gly Leu Val Leu Asp Gln Asp Asn Gln Phe Asp Gln Thr
145                 150                 155                 160

Glu Ala Arg Leu Ala Ser Trp Leu Glu Glu Ile Lys Arg Thr Val Leu
                165                 170                 175

<210> SEQ ID NO 27
<211> LENGTH: 170
<212> TYPE: PRT
<213> ORGANISM: A. variabilis

<400> SEQUENCE: 27

Met Ser Lys Lys Ile Gly Leu Phe Tyr Gly Thr Gln Thr Gly Lys Thr
 1                   5                  10                  15

Glu Ser Val Ala Glu Ile Ile Arg Asp Glu Phe Gly Asn Asp Val Val
            20                  25                  30

Thr Leu His Asp Val Ser Gln Ala Glu Val Thr Asp Leu Asn Asp Tyr
            35                  40                  45

Gln Tyr Leu Ile Ile Gly Cys Pro Thr Trp Asn Ile Gly Glu Leu Gln
        50                  55                  60

Ser Asp Trp Glu Gly Leu Tyr Ser Glu Leu Asp Asp Val Asp Phe Asn
 65                  70                  75                  80

Gly Lys Leu Val Ala Tyr Phe Gly Thr Gly Asp Gln Ile Gly Tyr Ala
                85                  90                  95

Asp Asn Phe Gln Asp Ala Ile Gly Ile Leu Glu Glu Lys Ile Ser Gln
            100                 105                 110

Arg Gly Gly Lys Thr Val Gly Tyr Trp Ser Thr Asp Gly Tyr Asp Phe
            115                 120                 125

Asn Asp Ser Lys Ala Leu Arg Asn Gly Lys Phe Val Gly Leu Ala Leu
            130                 135                 140

Asp Glu Asp Asn Gln Ser Asp Leu Thr Asp Asp Arg Ile Lys Ser Trp
145                 150                 155                 160

Val Ala Gln Leu Lys Ser Glu Phe Gly Leu
                165                 170

<210> SEQ ID NO 28
<211> LENGTH: 170
<212> TYPE: PRT
<213> ORGANISM: A. nidulans

<400> SEQUENCE: 28

```
Met Ala Lys Ile Gly Leu Phe Tyr Gly Thr Gln Thr Gly Val Thr Gln
 1               5                  10                  15

Thr Ile Ala Glu Ser Ile Gln Gln Glu Phe Gly Gly Glu Ser Ile Val
            20                  25                  30

Asp Leu Asn Asp Ile Ala Asn Ala Asp Ala Ser Asp Leu Asn Ala Tyr
        35                  40                  45

Asp Tyr Leu Ile Ile Gly Cys Pro Thr Trp Asn Val Gly Glu Leu Gln
    50                  55                  60

Ser Asp Trp Glu Gly Ile Tyr Asp Asp Leu Asp Ser Val Asn Phe Gln
65                  70                  75                  80

Gly Lys Lys Val Ala Tyr Phe Gly Ala Gly Asp Gln Val Gly Tyr Ser
                85                  90                  95

Asp Asn Phe Gln Asp Ala Met Gly Ile Leu Glu Glu Lys Ile Ser Ser
            100                 105                 110

Leu Gly Ser Gln Thr Val Gly Tyr Trp Pro Ile Glu Gly Tyr Asp Phe
        115                 120                 125

Asn Glu Ser Lys Ala Val Arg Asn Asn Gln Phe Val Gly Leu Ala Ile
    130                 135                 140

Asp Glu Asp Asn Gln Pro Asp Leu Thr Lys Asn Arg Ile Lys Thr Trp
145                 150                 155                 160

Val Ser Gln Leu Lys Ser Glu Phe Gly Leu
                165                 170

<210> SEQ ID NO 29
<211> LENGTH: 90
<212> TYPE: PRT
<213> ORGANISM: Artificial sequence
<220> FEATURE:
<223> OTHER INFORMATION: Consensus sequence

<400> SEQUENCE: 29

Met Ala Lys Ile Gly Phe Phe Gly Thr Asp Thr Gly Thr Ile Ala Ile
 1               5                  10                  15

Gly Asp Val Ala Asp Tyr Leu Ile Leu Gly Pro Thr Gly Glu Leu Gln
            20                  25                  30

Asp Trp Glu Phe Leu Asp Phe Gly Lys Thr Val Ala Leu Phe Gly Gly
        35                  40                  45

Asp Gln Tyr Asn Phe Ala Leu Glu Arg Gly Val Gly Trp Pro Gly Tyr
    50                  55                  60

Phe Ser Lys Ala Phe Val Gly Leu Ala Asp Glu Asp Asn Gln Asp Leu
65                  70                  75                  80

Thr Glu Arg Ile Trp Val Gln Lys Phe Leu
                85                  90

<210> SEQ ID NO 30
<211> LENGTH: 45
<212> TYPE: DNA
<213> ORGANISM: Helicobacter pylori
<220> FEATURE:
<221> NAME/KEY: CDS
<222> LOCATION: (1)...(45)

<400> SEQUENCE: 30 gtt ctt tcg ctt aat ctt tat aag ccc tat att tta ggg ctt ttt        45
Val Leu Ser Leu Asn Leu Tyr Lys Pro Tyr Ile Leu Gly Leu Phe
 1               5                  10                  15

<210> SEQ ID NO 31
```

```
<211> LENGTH: 15
<212> TYPE: PRT
<213> ORGANISM: Helicobacter pylori

<400> SEQUENCE: 31

Val Leu Ser Leu Asn Leu Tyr Lys Pro Tyr Ile Leu Gly Leu Phe
 1               5                  10                  15
```